United States Patent
Pazenok et al.

(10) Patent No.: US 8,044,231 B2
(45) Date of Patent: Oct. 25, 2011

(54) METHOD FOR PRODUCING DIHALO ACETOACETIC ALKYL ESTERS

(75) Inventors: Sergii Pazenok, Solingen (DE); Norbert Lui, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 259 days.

(21) Appl. No.: 12/524,923

(22) PCT Filed: Jan. 22, 2008

(86) PCT No.: PCT/EP2008/000438
§ 371 (c)(1),
(2), (4) Date: Aug. 20, 2009

(87) PCT Pub. No.: WO2008/092583
PCT Pub. Date: Aug. 7, 2008

(65) Prior Publication Data
US 2010/0121095 A1    May 13, 2010

(30) Foreign Application Priority Data
Feb. 2, 2007 (DE) .......... 10 2007 005 296

(51) Int. Cl.
*C07C 69/66* (2006.01)
(52) U.S. Cl. ................................ 560/174
(58) Field of Classification Search .......... None
See application file for complete search history.

(56) References Cited

U.S. PATENT DOCUMENTS

| 5,789,624 A | 8/1998 | Unruh et al. |
| 2006/0149091 A1 | 7/2006 | Gallenkamp et al. |
| 2008/0004465 A1 | 1/2008 | Walter et al. |

OTHER PUBLICATIONS

International Search Report of PCT/EP2008/000438, dated Jul. 29, 2008 (5 pages).
Tice et al. "Regiocontrolled synthesis of 3-substituted-6-trifluoromethyl-4(3H)-pyrimidinones," Tetrahedron, 2001, 57, pp. 2689-2700.
Dolence et al. "Synthesis of Analogs of Farnesyl Diphosphate," Tetrahedron, vol. 52, No. 1, pp. 119-130, 1996, copyright 1995 Elsevier Science Ltd.
Jones "The Synthesis of Ethyl Ethoxymethyleneoxalacetate and Related Compounds," Journal of the American Chemical Society, 1951, 73 (8), pp. 3684-3686.
Petrov, et al. "1,1,2,2-Tetrafluoroethyl-N,N-dimethylamine: a new selective fluorinating agent," Journal of Fluorine Chemical, 109 (2001) pp. 25-31.
Dmowski "Replacement of Sulfur by Fluorine," Chemistry of Organic Fluorine Compounds II, 1995, American Chemical Society, pp. 263-270.

*Primary Examiner* — Paul A Zucker
(74) *Attorney, Agent, or Firm* — Baker Donelson Bearman, Caldwell & Berkowitz, PC

(57) ABSTRACT

The invention relates to a process for preparing alkyl dihaloacetoacetates of the formula (I) by reacting α,α-dihaloamines of the formula (III) with acetic esters of the formula (II) in the presence of bases.

18 Claims, No Drawings

METHOD FOR PRODUCING DIHALO ACETOACETIC ALKYL ESTERS

CROSS REFERENCE TO RELATED APPLICATIONS

This application is a §371 National Stage Application of PCT/EP2008/000438 filed Jan. 22, 2008 which claims priority from German Application 10 2007 005 296.2 filed Feb. 2, 2007.

BACKGROUND OF THE INVENTION

1. Field of the Invention

The invention relates to a process for preparing alkyl dihaloacetoacetates of the formula (I) by reacting α,α-dihaloamines of the formula (III) with carboxylic esters of the formula (II) in the presence of bases.

2. Description of Related Art

Alkyl difluoroacetoacetates are important synthesis units for preparing active agrochemical ingredients, especially for preparing pyrazolylcarboxanilides.

Tetrahedron 2001, 57, 2689-2700 discloses that 4,4-difluoroacetoacetic esters can be obtained by reacting ethyl difluoroacetoacetate with ethyl acetate in the presence of sodium hydride (NaH). The yield of this reaction is very unsatisfactory at 25%. Moreover, Tetrahedron 1996, 52, 119-130 states that 4,4-difluoroacetoacetic esters can be prepared by reacting ethyl difluoroacetate with ethyl bromoacetate in the presence of Zn.

WO-A-2005/003077 teaches a three-stage process for preparing alkyl difluoroacetoacetates proceeding from chlorodifluoroacetoacetic esters by reducing the chlorine atom with trialkoxyphosphines (P(OAlk)$_3$), which is also known as the Perkow reaction.

WO-A-2006/005612 teaches a process for preparing 4,4-difluoro-3-oxobutyric esters by reacting 2,2-difluoro-N,N-dialkylacetamide with acetic esters in the presence of bases. The alkyl 4,4-difluoro-3-oxobutyrate is subsequently, as described in JACS, 73, 3684 (1951), reacted with trimethyl orthoformate and acetic anhydride to give ethyl (2-ethoxymethylene)-4,4-difluoromethylacetoacetate which, according to U.S. Pat. No. 5,489,624, can be converted using methylhydrazine to ethyl 3-difluoromethyl-1-methyl-4-pyrazolecarboxylate. The route described firstly includes a multitude of reaction steps, and the 2,2-difluoro-N,N-dialkylacetamide used is secondly not commercially available and can be obtained only in small yields of approx. 70% by fluorinating 2,2-dichloro-N,N-dialkylacetamide.

The processes described before in the prior art have the disadvantage that the difluorocarbonyl halides, haloalkylcarboxylic anhydrides and haloacrylic esters used are expensive, cause corrosion problems and/or can be purified only with a high level of technical complexity.

SUMMARY OF THE INVENTION

It is therefore an object of the present invention to provide a simpler and more economically viable process for preparing alkyl dihaloacetoacetates.

The object is achieved, surprisingly, by a process for preparing alkyl dihaloacetoacetates of the formula (I)

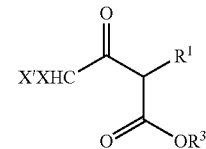

in which
X is fluorine, chlorine or CF$_3$,
X' is fluorine, chlorine or bromine,
R$^1$ is selected from H, C$_{1-12}$-alkyl radicals, C$_{5-18}$-aryl, chlorine, bromine and fluorine and
R$^3$, independently of R$^1$, is selected from C$_{1-12}$-alkyl, C$_{5-18}$-aryl or C$_{7-19}$-arylalkyl radicals,
by reacting α,α-dihaloamines of the formula (III)

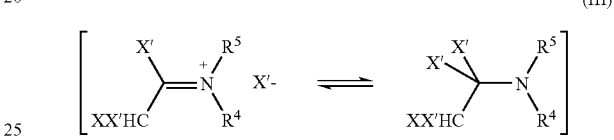

in which
R$^4$ is selected from C$_{1-12}$-alkyl radicals, C$_{5-18}$-aryl radicals or C$_{7-19}$-arylalkyl radicals,
R$^5$, independently of R$^4$, is selected from C$_{1-12}$-alkyl radicals, C$_{5-18}$-aryl radicals or C$_{7-19}$-arylalkyl radicals,
with carboxylic esters of the formula (II)

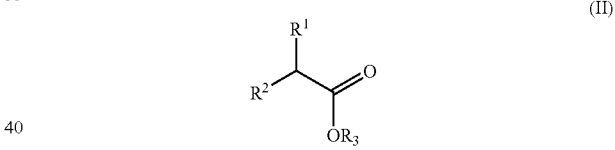

in which
R$^2$ is selected from hydrogen, C$_{1-12}$-alkyl radicals, C$_{5-18}$-aryl, chlorine, bromine and fluorine.

DETAILED DESCRIPTION OF A PREFERRED EMBODIMENT

In a preferred embodiment of the present invention,
X is selected from fluorine, chlorine or CF$_3$;
X' is selected from fluorine or chlorine;
R$^1$ is selected from C$_{1-4}$-alkyl radicals;
R$^2$, independently of R$^1$, is selected from C$_{1-4}$-alkyl radicals;
R$^3$, independently of R$^1$, is selected from C$_{1-4}$-alkyl;
R$^4$ is selected from C$_{1-4}$-alkyl radicals;
R$^5$, independently of R$^4$, is selected from C$_{1-4}$-alkyl radicals.

In a particularly preferred embodiment of the present invention,
X is selected from fluorine or chlorine;
X' is fluorine;
R$^1$ is selected from hydrogen or fluorine;
R$^2$ is hydrogen;
R$^3$ is selected from methyl or ethyl;
R$^4$ is selected from methyl or ethyl;

$R^5$ is selected from methyl or ethyl.

Further embodiments of the present invention can be taken from the dependent claims and the description.

The process according to the invention can be illustrated by the following scheme (I):

Scheme (I)

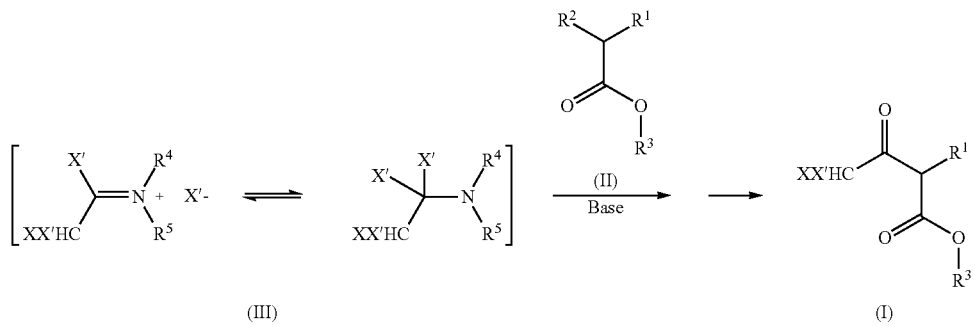

GENERAL DEFINITIONS

In connection with the present invention, the term "halogens" (X) encompasses those elements which are selected from the group consisting of fluorine, chlorine, bromine and iodine, preference being given to using fluorine, chlorine and bromine and particular preference to using fluorine and chlorine.

Optionally substituted radicals may be mono-or polysubstituted, where the substituents may be the same or different in the case of multiple substitutions.

In connection with the present invention, alkyl radicals, unless defined differently, are linear, branched or cyclic hydrocarbon radicals which may optionally have one, two or more single or double unsaturations or one, two or more heteroatoms which are selected from O, N, P and S. In addition, the inventive alkyl radicals may optionally be substituted by further groups which are selected from —X, —OR', —SR', —NR'$_2$, —SiR'$_3$, —COOR', —CN and —CONR$_2$' groups, where R' may be hydrogen or a $C_{1-4}$-alkyl group.

The definition "$C_1$-$C_{12}$-alkyl" encompasses the largest range defined herein for an alkyl radical. Specifically, this definition encompasses, for example, the meanings of methyl, ethyl, n-, isopropyl, n-, iso-, sec-and t-butyl, n-pentyl, n-hexyl, 1,3-dimethylbutyl, 3,3-dimethylbutyl, n -heptyl, n-nonyl, n-decyl, n-undecyl, n-dodecyl.

In connection with the present invention, unless defined differently, aryl radicals are cyclic aromatic hydrocarbon radicals which may have one, two or more heteroatoms which are selected from O, N, P and S and may optionally be substituted by further groups which are selected from —X, —OR', —SR', —NR'$_2$, —SiR'$_3$, —COOR', —CN and —CONR$_2$' groups, where R' may be hydrogen or a $C_{1-4}$-alkyl group.

The definition "$C_{5-18}$-aryl" encompasses the largest range for an aryl radical having 5 to 18 skeletal carbon atoms defined herein. Specifically, this definition encompasses, for example, the meanings of cyclopentenyl, phenyl, cycloheptatrienyl, cyclooctatetraenyl, naphthyl and anthracenyl.

In connection with the present invention, unless defined differently, arylalkyl radicals are cyclic aromatic hydrocarbon radicals which may have one, two or more heteroatoms which are selected from O, N, P and S and which have at least one $C_{1-8}$-alkyl side chain which may optionally form a four-, five-or six-membered ring with a further side chain and may optionally be substituted by further groups which are selected from —X, —OR', —SR', —NR'$_2$, —SiR'$_3$, —COOR', —CN and —CONR$_2$' groups, where R' may be hydrogen or a $C_{1-4}$-alkyl group.

The definition "$C_{7-19}$-arylalkyl" radical encompasses the largest range for an arylalkyl radical having a total of 7 to 19 carbon atoms in the skeleton and side chain defined herein. Specifically, this definition encompasses, for example, the meanings of tolyl, o-xylyl, m-xylyl, p-xylyl and ethylphenyl.

The inventive compounds may optionally be present as mixtures of different possible isomeric forms, especially of stereoisomers, for example E and Z, threo and erythro, and also optical isomers, but if appropriate also of tautomers. Both the E and the Z isomers, and also the threo and erythro isomers, and also the optical isomers, any mixtures of these isomers, and the possible tautomeric forms are claimed.

Carboxylic Esters

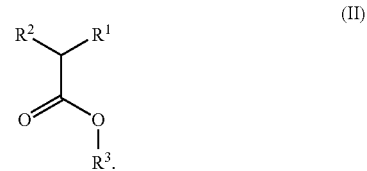

In the esters, the $R^2$ and $R^3$ radicals are each independently selected from H, $C_{1-12}$-alkyl, $C_{5-18}$-aryl or $C_{7-19}$-arylalkyl radicals, preferably from $C_{2-8}$-alkyl radicals, more preferably from $C_{3-6}$-alkyl radicals.

Examples of suitable carboxylic esters are methyl acetate, ethyl acetate, ethyl fluoroacetate, ethyl bromoacetate, ethyl propionate, ethyl phenylacetate, ethyl benzoate.

According to the present invention, acetic esters are preferred, ethyl acetate being particularly preferred.

α,α-Dihaloamines

The α,α-dihaloamines used in accordance with the present invention are compounds of the general formula (III)

in which
R⁴ is selected from $C_{1-12}$-alkyl, $C_{5-18}$-aryl or $C_{7-19}$-arylalkyl radicals, preferably from $C_{2-8}$-alkyl radicals, more preferably from $C_{3-6}$-alkyl radicals;
R⁵, independently of R⁴, is selected from $C_{1-12}$-alkyl, $C_{5-18}$-aryl or $C_{7-19}$-arylalkyl radicals, preferably from $C_{2-8}$-alkyl radicals, more preferably from $C_{3-6}$-alkyl radicals;
X is $CF_3$, fluorine or chlorine, preference being given to fluorine, and
X' is fluorine, chlorine or bromine, preference being given to fluorine.

The compounds are obtainable according to Petrov et al. in Journal of Fluorine Chemistry 109 (2001) 25-31 and Dmowski et al. in Chemistry of Organic Fluorine Compounds II, A Critical Review, ACS, Washington D.C. (1995) 263 by reaction of fluorinated/halogenated alkenes with secondary amines, and are sold commercially, for example, by DuPont.

The α-haloamines used with preference in accordance with the present invention are, for example, selected from the group consisting of 1,1,2,2-tetrafluoroethyl-N,N-dimethylamine, 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa reagent), 1,1,2-trifluoro-2-chloroethyl-N,N-dimethylamine and 1,1,2-trifluoro-2-chloroethyl-N,N-diethylamine (Yarovenko reagent), preference being given to 1,1,2,2-tetrafluoroethyl-N,N-dimethylamine and 1,1,2,2-tetrafluoroethyl-N,N-diethylamine, and particular preference to 1,1,2,2-tetrafluoroethyl-N,N-dimethylamine.

It is possible to prepare chloroamines or salts thereof (analogously to the Vilsmeier complex) from, for example, N,N-dimethyldifluoroacetamide and, for example, oxalyl chloride, phosgene or $POCl_3$:

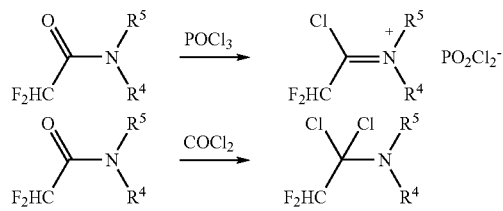

Bases

The α,α-dihaloamines of the formula (III) are reacted with the carboxylic esters of the formula (II) typically in the presence of bases, which deprotonate the carboxylic esters in the α-position to the carbonyl group.

According to the present invention, suitable bases are all of those which have sufficient basicity to deprotonate the carboxylic esters. Examples include alkali metal hydroxides, for example lithium hydroxide, sodium hydroxide or potassium hydroxide, alkali metal alkoxides, for example NaOMe, NaOEt, NaOt-Bu, KOt-Bu, hydrides, for example NaH, KH, alkyllithium reagents, for example n-BuLi or t-BuLi, LiN(iPr)₂, Grignard reagents, for example $CH_3MgCl$; phosphazenes and 1,8-diazabicyclo[5.4.0]undecene (DBU).

The α,α-dihaloamines are reacted with the carboxylic esters typically at temperatures of −50 to 60° C., preferably of −20 to 40° C., more preferably of −10 to 30° C.

The reaction can be effected under reduced pressure, under standard pressure or under high pressure, preferably under standard pressure.

The reaction can be performed in bulk or in a solvent. Preference is given to performing the reaction in a solvent. Suitable solvents are, for example, selected from the group consisting of aliphatic and aromatic hydrocarbons, for example n-hexane, benzene or toluene, which may be substituted by fluorine and chlorine atoms, for example methylene chloride, dichloroethane, fluorobenzene, chlorobenzene or dichlorobenzene; ethers, for example diethyl ether, diphenyl ether, methyl tert-butyl ether, isopropyl ethyl ether, dioxane, diglyme, dimethyl glycol, dimethoxyethane (DME) or THF; nitriles such as methylnitrile, butylnitrile or phenylnitrile; amides such as dimethylformamide (DMF) or N-methylpyrrolidone (NMP) or mixtures of such solvents, particular preference being given to THF, DME, diethyl ether. The reaction can be effected in an excess of carboxylic ester (e.g. in ethyl acetate).

The base and the carboxylic ester are preferably used in equimolar amounts. Alternatively, the base can also be used in excess. The ratio of base:carboxylic ester is, in accordance with the invention, between 1.5:1 and 0.9:1, preferably between 1.4:1, more preferably between 1.3:1, and 1.05:1.

In a preferred embodiment of the process according to the invention, the carboxylic ester is initially charged in bulk or dissolved in a suitable solvent and admixed gradually with the base and then reacted with the α,α-dihaloamine Owing to the hydrolysis sensitivity of the α,α-dihaloamines, the reaction should be performed in anhydrous apparatus under inert gas atmosphere.

The invention will be illustrated in detail with reference to the working examples which follow, but without restricting it thereto.

PREPARATION EXAMPLES

Example 1

Preparation of Ethyl Difluoroacetoacetate

An initial charge of 48 g of ethyl acetate was admixed at RT with a 10% solution of 32.4 g of sodium ethoxide in ethanol. The mixture was stirred at RT for 1 h and then admixed with 36 g of 1,1,2,2-tetrafluoroethyldimethylamine. Subsequently, the solution was stirred at 30° C. for 2 h, admixed with $H_2O$ and adjusted to pH 5. After extraction with ethyl acetate and subsequent distillation, 27 g (65%) of ethyl difluoroacetoacetate (boiling point 90-94° C./100 mbar) were obtained.

Example 2

Analogous to Example 1, except that sodium hydride was used in place of sodium ethoxide. The yield achieved is 79%.

Example 3

Analogous to Example 1, except that 1,1-dichloro-2,2-difluoroethyldimethylamine (prepared from N,N-dimethyldifluoroacetamide and oxalyl chloride at 80° C.) was used. The yield achieved is 63%.

The invention claimed is:
1. A process for preparing an alkyl dihaloacetoacetate of formula (I)

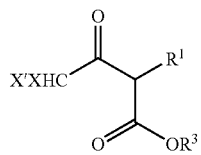

in which
X is fluorine, chlorine or $CF_3$,
X' is fluorine, chlorine or bromine,
$R^1$ is selected from H, $C_{1-12}$-alkyl radicals, $C_{5-18}$-aryl, Cl, bromine and fluorine and
$R^3$, independently of $R^1$, is selected from $C_{1-12}$-alkyl, $C_{5-18}$-aryl or $C_{7-19}$-arylalkyl radicals, by reacting α,α-dihaloamines of the formula (III)

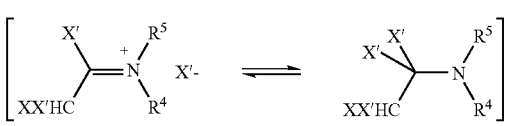

in which
$R^4$ is selected from $C_{1-12}$-alkyl radicals, $C_{5-18}$-aryl radicals or $C_{7-19}$-arylalkyl radicals,
$R^5$, independently of $R^4$, is selected from $C_{1-12}$-alkyl radicals, $C_{5-18}$-aryl radicals or $C_{7-19}$-arylalkyl radicals,
with a carboxylic ester of the formula (II)

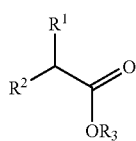

in which
$R^2$ is selected from H, $C_{1-12}$-alkyl radicals, $C_{5-18}$-aryl, Cl, bromine and fluorine.

2. A process according to claim 1, wherein
X is selected from fluorine, chlorine or $CF_3$;
X' is selected from fluorine or Cl;
$R^1$ is selected from $C_{1-4}$-alkyl radicals;
$R^2$, independently of $R^1$, is selected from $C_{1-4}$-alkyl radicals;
$R^3$, independently of $R^1$, is selected from $C_{1-4}$-alkyl;
$R^4$ is selected from $C_{1-4}$-alkyl radicals and
$R^5$, independently of $R^4$, is selected from $C_{1-4}$-alkyl radicals.

3. A process according to claim 1, wherein
X is selected from fluorine or chlorine;
X' is fluorine;
$R^1$ is selected from hydrogen or fluorine;
$R^2$ is hydrogen;
$R^3$ is selected from methyl or ethyl;
$R^4$ is selected from methyl or ethyl;
$R^5$ is selected from methyl or ethyl.

4. A process according to claim 1, wherein said process is effected in the presence of a base.

5. A process according to claim 1, wherein the α,α-dihaloamine is selected from the group consisting of 1,1,2,2-tetrafluoroethyl-N,N-dimethylamine, 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N -diethylamine, 1,1,2-trifluoro-2-chloroethyl-N,N-dimethylamine and 1,1,2-trifluoro-2-chloroethyl-N,N-diethylamine.

6. A process according to claim, wherein the base is at least the selected from the group consisting of alkali metal hydroxides, alkali metal alkoxides, hydrides, alkyllithium reagents and Grignard reagents.

7. A process according to claim 1, wherein the carboxylic ester is selected from methyl acetate, ethyl acetate, ethyl fluoroacetate, ethyl bromoacetate, ethyl propionate, ethyl phenylacetate and ethyl benzoate.

8. A process according to claim 2, wherein
X is selected from fluorine or chlorine;
X' is fluorine;
$R^1$ is selected from hydrogen or fluorine;
$R^2$ is hydrogen;
$R^3$ is selected from methyl or ethyl;
$R^4$ is selected from methyl or ethyl;
$R^5$ is selected from methyl or ethyl.

9. A process according to claim 2, wherein said process is effected in the presence of a base.

10. A process according to claim 3, wherein said process is effected in the presence of a base.

11. A process according to claim 2, wherein the α,α-dihaloamine is selected from the group consisting of 1,1,2,2-tetrafluoroethyl-N,N-dimethylamine, 1,1,2,2-tetrafluoroethyl-N,N -diethylamine, 1,1,2-trifluoro-2-(trifluoromethyl)ethyl-N,N-dimethylamine, 1,1,2-trifluoro-2-(trifluoromethyl)ethyl-N,N-diethylamine, 1,1,2-trifluoro-2-chloroethyl-N,N-dimethylamine and 1,1,2-trifluoro-2-chloroethyl-N,N-diethylamine.

12. A process according to claim 3, wherein the α,α-dihaloamine is selected from the group consisting of 1,1,2,2-tetrafluoroethyl-N,N-dimethylamine, 1,1,2,2-tetrafluoroethyl-N,N -diethylamine, 1,1,2-trifluoro-2-(trifluoromethyl)ethyl-N,N-dimethylamine, 1,1,2-trifluoro-2-(trifluoromethyl)ethyl-N,N-diethylamine, 1,1,2-trifluoro-2-chloroethyl-N,N-dimethylamine and 1,1,2-trifluoro-2-chloroethyl-N,N-diethylamine.

13. A process according to claim 4, wherein the α,α-dihaloamine is selected from the group consisting of 1,1,2,2-tetrafluoroethyl-N,N-dimethylamine, 1,1,2,2-tetrafluoroethyl-N,N -diethylamine, 1,1,2-trifluoro-2-(trifluoromethyl)ethyl-N,N-dimethylamine, 1,1,2-trifluoro-2-(trifluoromethyl)ethyl-N,N-diethylamine, 1,1,2-trifluoro-2-chloroethyl-N,N-dimethylamine and 1,1,2-trifluoro-2-chloroethyl-N,N-diethylamine.

14. A process according to claim 2, wherein the carboxylic ester is selected from methyl acetate, ethyl acetate, ethyl fluoroacetate, ethyl bromoacetate, ethyl propionate, ethyl phenylacetate and ethyl benzoate.

15. A process according to claim 3, wherein the carboxylic ester is selected from methyl acetate, ethyl acetate, ethyl fluoroacetate, ethyl bromoacetate, ethyl propionate, ethyl phenylacetate and ethyl benzoate.

16. A process according to claim 4, wherein the carboxylic ester is selected from methyl acetate, ethyl acetate, ethyl fluoroacetate, ethyl bromoacetate, ethyl propionate, ethyl phenylacetate and ethyl benzoate.

17. A process according to claim 5, wherein the carboxylic ester is selected from methyl acetate, ethyl acetate, ethyl fluoroacetate, ethyl bromoacetate, ethyl propionate, ethyl phenylacetate and ethyl benzoate.

18. A process according to claim 6, wherein the carboxylic ester is selected from methyl acetate, ethyl acetate, ethyl fluoroacetate, ethyl bromoacetate, ethyl propionate, ethyl phenylacetate and ethyl benzoate.

* * * * *